United States Patent [19]

Hitzel et al.

[11] 4,132,795

[45] Jan. 2, 1979

[54] BENZENESULFONYL UREAS AND THEIR USE FOR THE TREATMENT OF DIABETES MELLITUS

[75] Inventors: Volker Hitzel, Hofheim am Taunus; Rudi Weyer, Kelkheim; Werner Pfaff, Hofheim am Taunus; Karl Geisen, Frankfurt am Main, all of Fed. Rep. of Germany

[73] Assignee: Hoechst Aktiengesellschaft, Frankfurt am Main, Fed. Rep. of Germany

[21] Appl. No.: 797,132

[22] Filed: May 16, 1977

[30] Foreign Application Priority Data

May 18, 1976 [DE] Fed. Rep. of Germany ....... 2621958

[51] Int. Cl.$^2$ ................. C07D 213/56; A61K 31/455
[52] U.S. Cl. .................................... 424/266; 546/155; 546/156; 546/285; 546/291
[58] Field of Search .................. 260/294.8 F, 294.8 B, 260/294.8 C; 424/266

[56] References Cited

U.S. PATENT DOCUMENTS

| 3,919,245 | 11/1975 | Weyer et al. ................ 260/294.8 F |
| 4,066,639 | 1/1978 | Weber et al. ................ 260/239 BF |

*Primary Examiner*—Alan L. Rotman
*Attorney, Agent, or Firm*—Curtis, Morris & Safford

[57] ABSTRACT

Benzenesulfonyl ureas of the formula

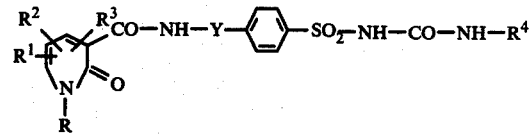

in which R, R$^1$, R$^2$, R$^3$, R$^4$ and Y have the defined meanings, and the salts thereof, process for preparing them, pharmaceutical preparations containing them and their use for lowering the blood sugar level.

8 Claims, No Drawings

BENZENESULFONYL UREAS AND THEIR USE FOR THE TREATMENT OF DIABETES MELLITUS

This invention provides benzenesulfonyl ureas of the formula

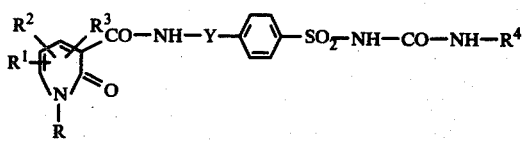

which have blood sugar reducing properties as such and in the form of their salts and are distinguished by a strong and long lasting reduction of the blood sugar level.

In the aforesaid formula the individual radicals have the following means:

R represents alkyl, alkoxyalkyl, or alkenyl each having up to 6 carbon atoms, cycloalkyl, cycloalkenyl, alkylcycloalkyl, alkylcycloalkenyl, cycloalkylalkyl, cycloalkenylalkyl, alkylcycloalkylalkyl, alkylcycloalkenylalkyl each having from 5 to 9 carbon atoms, phenyl optionally mono- or disubstituted by alkyl or alkoxy each having up to 4 carbon atoms, or by halogen, phenylalkyl having up to 3 carbon atoms in the alkyl moiety and optionally mono- or disubstituted in the phenyl radical by alkyl or alkoxy having each up to 4 carbon atoms, or by halogen, $R^1$, $R^2$, $R^3$ stand for hydrogen, alkyl, alkoxy each having at most 2 carbon atoms, halogen, $R^1$ and $R^2$ together may also represent

in 5,6-position, optionally substituted by halogen or methyl,

Y is alkylene having 2 or 3 carbon atoms, preferably $-CH_2-CH_2-$ $R^4$ represents alkyl having from 3 to 6 carbon atoms, cycloalkyl, alkylcycloalkyl, cycloalkylalkyl, cycloalkenyl, alkylcycloalkenyl each having from 5 to 9 carbon atoms, $C_1$ to $C_2$-alkylcyclopentylmethyl, cyclohexenylmethyl, chlorocyclohexyl, bicycloheptenylmethyl, bicycloheptylmethyl, bicycloheptenyl, bicycloheptyl, nortricyclyl, adamantyl, benzyl.

Preferred compounds are those in which R represents an alkyl radical and especially the butyl radical and $R^1$, $R^2$ and $R^3$ stand for hydrogen.

This invention also provides processes for the preparation of the aforesaid sulfonyl ureas, which comprise (a) reacting benzenesulfonyl-isocyantes, -carbamic acid esters, -thiolcarbamic acid esters, -ureas, -semicarbazides or -semicarbazones substituted in 4-position by the group

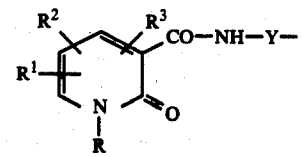

with an amine of the formula $R^4-NH_2$ or a salt thereof, or reacting sulfonamides of the formula

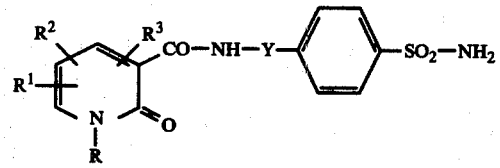

or the salts thereof with $R^4$-substituted isocyanates, carbamic acid esters, thiolcarbamic acid esters, carbamic acid halides, or ureas, (b) splitting correspondingly substituted benzenesulfonylisourea ethers, -isothiourea ethers, - parabanic acid or -haloformic acid amidines, (c) replacing the sulfur atom by oxygen in

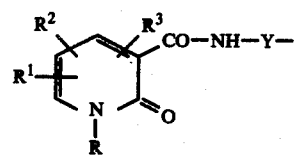

substituted benzenesulfonyl thioureas, (d) oxidizing corresponding benzene-sulfinyl or -sulfenyl ureas, (e) introducing the radical

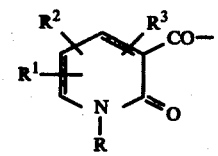

into benzenesulfonyl ureas of the formula

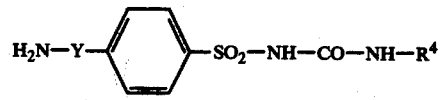

(f) reacting corresponding substituted benzenesulfonyl halides with $R^4$-substituted ureas or the alkali metal salts thereof or reacting with $N-R^4-N'$-hydroxyurea correspondingly substituted benzenesulfinic acid halides or sulfinic acids or the alkali metal salts thereof, in the latter case in the presence of acid condensing agents, and optionally treating the reaction products with alkaline agents to form the salts.

The benzenesulfonyl-carbamic acid esters or -thiolcarbamic acid esters may carry in the alcohol moiety an alkyl radical, and aryl radical or a heterocyclic radical. Owing to the fact that this radical is split off in the reaction, the chemical constitution thereof has no influence whatsoever on the character of the final product and, therefore, it can be chosen within wide limits. The same conditions are valid for the N-$R^4$-substituted carbamic acid esters and the corresponding thiolcarbamic acid esters.

As carbamic acid halides the chlorides are preferred.

The benzenesulfonyl ureas to be used in the process as starting material can be unsubstituted or monosubstituted and preferably disubstituted at the side of the urea molecule opposite to the sulfonyl group. Owing to the fact that these substituents are split off in the reaction with amines, they can be chosen within a wide range. Besides alkyl-, aryl-, acyl-, or heterocyclically substituted benzenesulfonyl ureas there can also be used benzenesulfonyl carbamoyl-imidazoles and analogous compounds or bisbenzenesulfonyl ureas which may carry a further substituent at one of the nitrogen atoms, for example methyl. Bis(benzenesulfonyl)ureas or N-benzenesulfonyl-N'-acyl ureas of this type can be treated, for example, with $R^4$-substituted amines and the salts obtained can be heated at elevated temperature, especially temperatures above 100° C.

Alternatively, $R^4$-substituted ureas or $R^4$-substituted ureas which are mono- and preferably disubstituted at the free nitrogen atom can be reacted with benzenesulfonamides substituted in 4-position by the group

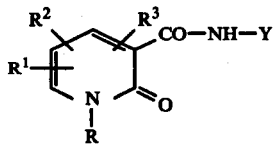

Suitable starting compounds of this group are, for example, N-cyclohexyl urea, the corresponding N'-acetyl, N'-nitro, N'-cyclohexyl, N',N'-diphenyl (in which the two phenyl radicals may be substituted or linked with each other either directly or via a bridge member such as —$CH_2$—, —NH—, —O—, or —S—), N'-methyl-N'-phenyl, N',N'-dicyclohexyl ureas as well as cyclohexyl-carbamoyl imidazoles, pyrazoles or triazoles and compounds of this type carrying, in the stead of cyclohexyl, another substituent coming within the definition of $R^4$.

The benzenesulfonyl parabanic acids, iso-urea ethers, isothiourea ethers, or haloformic acid amidines named as starting materials are suitably split by alkaline hydrolysis. Iso-urea ethers can also be split successfully in an acid medium.

To replace the sulfur atom in the urea grouping of correspondingly substituted benzenesulfonyl thioureas by an oxygen atom known methods can be used, for example a treatment with oxides or salts of heavy metals or by using oxidants, for example hydrogen peroxide, sodium peroxide, nitrous acid, or permanganates.

To desulfurize the thio-ureas they may also be treated with phosgene or phosphorus pentachloride. Chloroformic acid amidines or carbodiimides obtained as intermediaries can be transformed by suitable measures, for example saponification or the addition of water, into the benzenesulfonyl ureas.

The oxidation of benzenesulfinyl or benzenesulfenyl ureas is effected in a known manner, preferably with oxidants such as permanganate or hydrogen peroxide.

The introduce the acyl radical into a benzenesulfonyl urea according to process (e) a reactive derivative of an acid of the formula

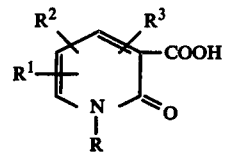

is preferably used. Suitable derivatives are, for example, halides or mixed anhydrides.

The reaction conditions of the processes according to the invention can be largely varied and adapted to the circumstances in each case. The reaction can be performed, for example, in the presence or absence of solvents, at room temperature or at elevated temperature.

Depending on the character of the starting compounds in some cases one or the other of the described processes may give a poor yield only of the desired benzenesulfonyl urea or it may be even unsuitable for its synthesis. In such a case, which is relatively seldom, the expert can easily synthesize the desired compound by one of the other described processes.

To determine the blood-sugar reducing action of the benzenesulfonyl ureas of the invention they are administered, in the form of the free compounds or the sodium salts thereof, in doses of 10 mg/kg to normally nourished rabbits and the blood-sugar value is measured over a prolonged period of time by the known method of Hagedorn-Jensen or with the aid of an autoanalyzer.

Acylaminoalkyl-benzenesulfonyl ureas carrying an amide group in the acyl radical have already been described in (cf. DOS No. 2,230,543) but these compounds are not characterized by such a strong and long lasting blood-sugar reducing effect as the compounds of the invention.

The benzenesulfonyl ureas of the present invention are preferably used for the manufacture of orally administrable preparations having a blood-sugar reducing effect in the treatment of Diabetes mellitus. They can be administered per se, in the form of their salts or in the presence of compounds bringing about salt formation, for example alkaline agents such as alkali metal or alkaline earth metal hydroxides, carbonates, or bicarbonates.

As medicinal preparations tablets are preferred containing, besides the active compound, the usual carrier materials and auxiliaries such as talc, starch, lactose, tragacanth, or magnesium stearate.

A preparation containing the described benzenesulfonyl ureas as active ingredient, for example a tablet or a powder, with or without additives, is preferably brought in a suitable dosage form. The chosen dose is adapted to the efficiency of the benzenesulfonyl urea used and the desired effect. In general, the dose per unit is in the range of from about 1 to 100 mg, preferably 5 to 20 mg, although higher or lower doses may also be used, which can be divided or multiplicated prior to administration.

The sulfonyl ureas of the invention can be used in the treatment of Diabetes mellitus either individually or in combination with other oral antidiabetics. Substances of this type are not only blood-sugar reducing sulfonyl ureas but also compounds of different chemical structure, for example biguanides, preferably phenylethyl biguanide or dimethyl biguanide.

The following examples are intended to illustrate the various processes suitable for the synthesis of the sulfonyl ureas of the invention.

EXAMPLE 1

N-[4-(β-<1,2-dihydro-1-methyl-2-oxo-nicotinamido>-ethyl)-benzenesulfonyl]-N'-cyclohexyl urea 2.9 g of 4-(β-<1,2-dihydro-1-methyl-2-oxo-nicotinamido>-ethyl)-benzenesulfonamide (melting point 235 - 237° C, prepared from 4-(β-aminoethyl)-benzenesulfonamide and the mixed anhydride of 1,2-dihydro-1-methyl-2-oxo-nicotinic acid in dilute acetone) in 100 ml acetone/100 ml dioxane were refluxed for 3 hours while stirring together with 2.5 g of pulverized potassium carbonate. 1.4 g of cyclohexyl-isocyanate were then added and the mixture was stirred for 8 hours at boiling temperature. The solvent was distilled off under reduced pressure, water was added to the residue, the whole was filtered, the filtrate acidified, the reaction product was filtered off with suction and recrystallized from dilute ethanol. The N-[4-(β-<1,2-dihydro-1-methyl-2-oxo-nicotinamido>-ethyl)-benzenesulfonyl]N'-cyclohexyl urea obtained melted at 210 - 212° C.

The following compounds were obtained in analogous manner: N-[4-(β-<1,2-dihydro-1-methyl-2-oxo-nicotinamido>-ethyl)-benzenesulfonyl]-N'-(4-methylcyclohexyl) urea melting at 225 - 227° C (from dilute ethanol); N[4-(β-<1,2-dihydro-1-methyl-2-oxo-nicotinamido>-ethyl)-benzenesulfonyl]-N'-isobutyl urea melting at 220 - 222° C (from ethanol); N-[4-(β-<1,2-dihydro-1-methyl-2-oxo-nicotinamido>-ethyl)-benzenesulfonyl]-N'-(4-ethylcyclohexyl) urea melting at 202 - 204° C (from ethanol).

EXAMPLE 2

N-[4-(β-<1-benzyl-1,2-dihydro-2-oxo-nicotinamido>-ethyl)-benzenesulfonyl]-N'-cyclohexyl urea 3.5 g of 4-(β-<1-benzyl-1,2-dihydro-2-oxo-nicotinamido>-ethyl)-benzenesulfonamide (melting point 196 - 198° C, prepared from 4-(β-aminoethyl)-benzenesulfonamide and the mixed anhydride of 1-benzyl-1,2-dihydro-2-oxo-nicotinic acid) in 70 ml acetone were refluxed for 3 hours while stirring together with 2.5 g of pulverized potash. 1.2 g of cyclohexyl isocyanate were then added and stirring was continued for 8 hours at boiling temperature. After cooling, the reaction mixture was filtered with suction, the solid matter was treated with warm water, filtered and the filtrate was acidified. The precipitated product was recrystallized from isopropanol. The N-[4-(β-<1-benzyl-1,2-dihydro-2-oxo-nicotinamido>-ethyl)-benzenesulfonyl]-N'-cyclohexyl urea melted at 192 - 194° C.

The following compounds were prepared in analogous manner: N-[4-(β-<1-benzyl-1,2-dihydro-2-oxo-nicotinamido>-ethyl)-benzenesulfonyl]-N'-(4-methylcyclohexyl) urea melting at 162 - 164° C (from isopropanol); N-[4-(β-<1-benzyl-1,2-dihydro-2-oxo-nicotinamido>-ethyl)-benzenesulfonyl]-N'-(4-ethylcyclohexyl)-urea melting at 164 - 166° C. (from dilute methanol).

EXAMPLE 3

N-[4-(β-<1-ethyl-1,2-dihydro-2-oxo-nicotinamido>-ethyl)-benzenesulfonyl]-N'-cyclohexyl urea 6.0 g of 4-(β-<1-ethyl-1,2-dihydro-2-oxo-nicotinamido>-ethyl)-benzenesulfonamide (melting point 215 - 216° C, prepared from 4-(β-aminoethyl)-benzenesulfonamide and 1-ethyl-1,2-dihydro-2-oxo-nicotinic acid chloride) were suspended in 60 ml acetone. After the addition of 8.55 ml 2N sodium hydroxide solution, the reaction mixture was cooled to 0° C, 2.35 g of cyclohexyl isocyanate in 5 ml acetone were added dropwise while stirring and stirring was continued for 1 hour at 0° C and for 4 hours at room temperature. The volume of the reaction mixture was then doubled by adding water, the mixture was filtered and the filtrate acidified with 2N hydrochloric acid. The precipitate was dissolved in dilute ammonia solution and precipitated again with dilute hydrochloric acid, stirred with sodium bicarbonate solution and recrystallized from methanol. The N-[4-(β-<1-ethyl-1,2-dihydro-2-oxo-nicotinamido>-ethyl)-benzenesulfonyl]-N'-cyclohexyl urea obtained in this manner melted at 189 - 190° C.

The following compounds were prepared in analogous manner: N-[4-(β-<1-ethyl-1,2-dihydro-2-oxo-nicotinamido>-ethyl)-benzenesulfonyl-N'-butyl urea melting at 170 - 171° C (from methanol/dioxane).

EXAMPLE 4

N-[4-(β-<1-ethyl-1,2-dihydro-2-oxo-nicotinamido>-ethyl)-benzenesulfonyl]-N'-cyclohexyl urea 2.0 g of 4-(β<1-ethyl-1,2-dihydro-2-oxo-nicotinamido>-ethyl)-benzenesulfonyl carbamic acid methyl ester (melting point 160 - 161° C, prepared from 4-(β-<1-ethyl-1,2-dihydro-2-oxo-nicotinamido]-ethyl)-benzenesulfonamide and chlorofomic acid methyl ester) in 30 ml of dioxane were gently boiled for 2 hours together with 0.5 g of cyclohexyl amine in a vessel with descending condenser. The solvent was then concentrated under reduced pressure, the residue was dissolved in dilute ammonia and precipitated with dilute hydrochloric acid, the reaction mixture was filtered with suction and the precipitate recrystallized from methanol. The N-[4-(β-<1-ethyl-1,2-dihydro-2-oxo-nicotinamido>-ethyl)-benzenesulfonyl]-N'-cyclohexyl urea obtained melted at 189 - 190° C.

The following compounds were prepared in analogous manner from 4-(β-<1-butyl-1,2-dihydro-2-oxo-nicotinamido>-ethyl)-benzenesulfonyl carbamic acid methyl ester (melting point 198 - 200° C):

N-[4-(β-<1-butyl-1,2-dihydro-2-oxo-nicotinamido>-ethyl)-benzenesulfonyl]-N'-cyclopentylmethyl urea melting at 153 - 155° C (from acetone);

N-[4-(β-<1-butyl-1,2-dihydro-2-oxo-nicotinamido>-ethyl)-benzenesulfonyl]-N'-cyclohexylmelthyl urea melting at 123 - 125° C (from ethyl acetate);

N-[4-(β-<1-butyl-1,2-dihydro-2-oxo-nicotinamido>-ethyl)-benzenesulfonyl]-N'-adamantyl urea melting at 182 - 184° C (from ethyl acetate/dimethyl formamide):

N-[4-(β-<1-butyl-1,2-dihydro-2-oxo-nicotinamido>-ethyl)-benzenesulfonyl]-N'-norbornylmethyl urea melting at 162 - 164° C (from ethyl acetate/methanol);

N-[4-(β-<1-butyl-1,2-dihydro-2-oxo-nicotinamido>-ethyl)-benzenesulfonyl]-N'-hexyl urea melting at 98 - 99° C (from ethyl acetate/methanol);

N-[4-(β-<1-butyl-1,2-dihydro-2-oxo-nicotinamido->ethyl)-benzenesulfonyl]-N'-(3-methylcyclopentylmethyl) urea melting at 118 - 119° C (from ethyl acetate/methanol);

N-[4-(β-<1-butyl-1,2-dihydro-2-oxo-nicotinamido>-ethyl)-benzenesulfonyl]-N'-norbornyl urea melting at 154 - 155° C (from methanol/dioxane);

N-[4-(β-<1-butyl-1,2-dihydro-2-oxo-nicotinamido>-ethyl)-benzenesulfonyl]-N'-(4-chlorocyclohexyl) urea melting at 133 – 135° C (from methanol);

N-[4-(β-<1-butyl-1,2-dihydro-2-oxo-nicotinamido>-ethyl)-benzenesulfonyl]-N'-Δ³-cyclohexenylmethyl urea melting at 122 – 124° C (from methanol).

EXAMPLE 5

N-[4-(β-<1-butyl-1,2-dihydro-2-oxo-nicotinamido>-ethyl)-benzenesulfonyl]-N'-cyclohexyl urea 7.6 g of 4-(β-<1-butyl-1,2-dihydro-2-oxo-nicotinamido>-ethyl)-benzenesulfonamide (melting point 162 – 163° C, prepared from 4-(β-aminoethyl)-benzenesulfonamide and 1-butyl-1,2-dihydro-2-oxo-nicotinic acid chloride in chloroform/soda solution) in 100 ml acetone and 50 ml dioxane were refluxed for 3 hours while stirring together with 5.5 g of pulverized potash. 2.5 g cyclohexyl isocyanate were then added and stirring was continued for 6 hours with reflux. After cooling, the reaction mixture was diluted with water, filtered and the filtrate acidified with 2N hydrochloric acid. The formed precipitate was filtered off with suction, dissolved in dilute ammonia and reprecipitated with dilute hydrochloric acid and finally recrystallized from methanol. The N-[4-(β-<1-butyl-1,2-dihydro-2-oxo-nicotinamido>-ethyl benzenesulfonyl]-N'-cyclohexyl urea obtained melted at 178 – 179° C.

The following compounds were prepared in analogous manner:

N-[4-(β-<1-butyl-1,2-dihydro-2-oxo-nicotinamido>-ethyl)-benzenesulfonyl]-N'-(4-methylcyclohexyl) urea melting at 159 – 160° C (from methane/dioxane);

N-[4-(β-<1-butyl-1,2-dihydro-2-oxo-nicotinamido>-ethyl)-benzenesulfonyl]-N'-butyl urea melting at 139 – 141° C (from methanol).

N-[4-(β-<1-butyl-1,2-dihydro-2-oxo-nicotinamido>-ethyl)-benzenesulfonyl]-N'-Δ³-cyclohexenyl urea melting at 169° C (from methanol/dimethyl formamide);

N-[4-(β-<1-butyl-1,2-dihydro-2-oxo-nicotinamido>-ethyl)-benzenesulfonyl]-N'-isobutyl urea melting at 141 – 142° C (from methanol/dimethyl formamide);

N-[4-(β-<1-butyl-1,2-dihydro-2-oxo-nicotinamido>-ethyl)-benzenesulfonyl]-N'-(4-ethylcyclohexyl) urea melting at 159 – 161° C (from methanol);

N-[4-(β-<1-butyl-1,2-dihydro-2-oxo-nicotinamido>-ethyl)-benzenesulfonyl]-N'-cycloheptyl urea melting at 149 – 151° C (from methanol);

N-[4-(β-<1-butyl-1,2-dihydro-2-oxo-nicotinamido>-ethyl)-benzenesulfonyl]-N'-cyclooctyl urea melting at 134 – 136° C (from methanol);

N-[4-(β-<1-butyl-1,2-dihydro-2-oxo-nicotinamido>-ethyl)-benzenesulfonyl]-N'-propyl urea melting at 149 – 151° C (from methanol);

N-[4-(β-<1butyl-1,2-dihydro-2-oxo-nicotinamido>-ethyl)-benzenesulfonyl]-N'-benzyl urea melting at 162 – 163° C (from methanol/dimethyl formamide).

EXAMPLE 6

N-[4-(β-<1,2-dihydro-1-(2-<3,4-dimethoxyphenyl>-ethyl-2-oxo-nicotinamido>-ethyl)-benzenesulfonyl]-N'-cyclohexyl urea 5.7 g of 1,2-dihydro-1-(2-<3,4-dimethoxyphenyl>-ethyl)-2-oxo-nicotinic acid were dissolved in 100 ml tetrahydrofurane together with 6.3 ml triethylamine, the solution was cooled to 0° C and 1.5 ml chloroformic acid methyl ester were added dropwise while stirring. Stirring was continued for 30 minutes at 0° C, 4.75 g of N-[4-(β-aminoethyl)-benzenesulfonyl]-N'-cyclohexyl urea were added in portions and stirring was continued for 4 hours at room temperature. The suspension obtained was concentrated under reduced pressure and the remaining residue taken up in dilute ammonia solution. After filtration, the filtrate was acidified with dilute hydrochloric acid. The reaction product was filtered off with suction and recrystallized from methanol/dioxane.

The N-[4-(β-<1,2-dihydro-1-(2-<3,4-dimethoxyphenyl>-ethyl)-2-oxo-nicotinamido>-ethyl)benzenesulfonyl]-N'-cyclohexyl urea melted at 199 – 201° C.

The following compounds were prepared in analogous manner: from 1,2-dihydro-1-(2-methoxy-ethyl)-2-oxo-nicotinic acid, N-[4-(β-<1,2-dihydro-1-(2-methoxyethyl)-2-oxo-nicotinamido>-ethyl)-benzenesulfonyl]-N'-cyclohexyl urea melting at 127 – 128° C (from methanol);

from 1,2-dihydro-4,6-dimethyl-1-(2-phenylethyl)-2-oxo-nicotinic acid,

N-[4-(β<1,2-dihydro-4,6-dimethyl-1-(2-phenylethyl)-2-oxo-nicotinamido>-ethyl)-benzenesulfonyl]-N'-cyclohexyl urea, melting at 185° C with decomposition, (from ethyl acetate/diisopropyl ether);

from 1-butyl-1,2-dihydro-4,6-dimethyl-2-oxo-nicotinic acid,

N-[4-(β-<1-butyl-1,2-dihydro-4,6-dimethyl-2-oxo-nicotinamido>-ethyl)-benzenesulfonyl]-N'-cyclohexyl urea melting at 148 – 150° C (from ethyl acetate/methanol);

from 1-ally-1,2-dihydro-2-oxo-nicotinic acid,

N-[4-(β-<1-allyl-1,2-dihydro-2-oxo-nicotinamido>-ethyl)-benzenesulfonyl]-N'-cyclohexyl urea melting at 155 – 157° C (from methanol);

from 1-benzyl-1,2-dihydro-2-oxo-quinoline-3-carboxylic acid,

N-[4-(β-<1-benzyl-1,2-dihydro-2-oxo-quinoline-3-carboxamido>-ethyl)-benzenesulfonyl]-N'-cyclohexyl urea melting at 190 – 193° C (from methanol).

EXAMPLE 7

N-[4-(β-<1-cyclohexylmethyl-1,2-dihydro-2-oxo-nicotinamido>-ethyl)-benzenesulfonyl]-N'-cyclohexyl urea 3.8 g of 1-cyclohexylmethyl-1,2-dihydro-2-oxo-nicotinic acid chlorine (raw melting point 116 –118° C, prepared from 1-cyclohexylmethyl-1,2-dihydro-2-oxo-nicotinic acid and thionyl chloride) were added in portins while stirring to a suspension of 4.75 g of N-[4-(β-aminoethyl)-benzenesulfonly]-N'-cyclohexyl urea in 50 ml pyridine. Stirring was continued for 3 hours at 50 – 60° C and the pyridine was distilled off under reduced pressure. The residue was taken up in dilute ammonia solution, the solution was filtered with the addition of charcoal and the filtrate was acidified. The precipitated N-[4-(β-<1-cyclohexylmethyl-1,2; -dihydro-2-oxo-nicotinamido>-ethyl)-benzenesulfonyl]-N'-cyclohexyl urea was recrystallized from methanol, its melting point was 138 – 140° C.

From 1,2-dihydro-1-(2-p-tolyl-ethyl)-2-oxo-nicotinic acid chloride (raw melting point 110 – 112° C) the following compound was prepared in analogous manner:

N-[4-(β-<1,2-dihydro-1(2-p-tolyl-ethyl)-2-oxo-nicotinamido>-ethyl)-benzenesulfonyl]-N'- cyclohexyl urea melting at 182 – 184° C (from methanol/dimethyl formamide).

What is claimed is:

1. A benzenesulfonyl urea of the formula

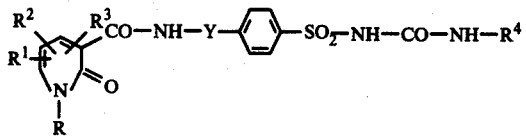

or a salt thereof in which

R represents alkyl, alkoxyalkyl, or alkenyl of up to 6 carbon atoms; cycloalkyl, cycloalkenyl, alkylcycloalkyl, alkylcycloalkenyl, cycloalkylalkyl, cycloalkenylalkyl, alkylcycloalkylalkyl, alkylcycloalkenylalkyl of from 5 to 9 carbon atoms; phenyl; phenyl mono- or disubstituted by alkyl or alkoxy of up to 4 carbon atoms, or by halogen; phenylalkyl having up to 3 carbon atoms in the alkyl moiety and optionally mono- or disubstituted in the phenyl radical by alkyl or alkoxy each having up to 4 carbon atoms, or by halogen;

$R^1$, $R^2$, $R^3$ stand for hydrogen, alkyl or alkoxy of up to two carbon atoms or halogen;

Y is alkylene of 2 or 3 carbon atoms, and $R^4$ represents alkyl of from 3 to 6 carbon atoms; cycloalkyl, alkylcycloalkyl, cycloalkylalkyl, cycloalkenyl, alkylcycloalkenyl or from 5 to 9 carbon atoms, $C_1$ to $C_2$-alkylcyclopentylmethyl, cyclohexenylmethyl, chlorocyclohexyl, bicycloheptenylmethyl, bicycloheptylmethyl, bicycloheptenyl, bicycloheptyl, nortricyclyl, adamantyl or benzyl.

2. A composition for the treatment of Diabetes mellitus which comprises an effective amount of a compound as defined in claim 1 and a pharmaceutical carrier.

3. The compound defined in claim 1 which is N-[-4-(β-<1-ethyl-1,2-dihydro-2-oxo-nicotinamido>-ethyl)-benzenesulfonyl]-N'-cyclohexyl urea.

4. The compound defined in claim 1 which is N-[4-(β-<1-butyl-1,2-dihydro-2-oxo-nicotinamido>-ethyl)-benzenesulfonyl]-N'-cyclohexyl urea.

5. The compound defined in claim 1 which is N-[4-(β-<1-ethyl-1,2-dihydro-2-oxo-nicotinamido>-ethyl)-benzenesulfonyl]-N'-(4-methylcyclohexyl)-urea.

6. The compound defined in claim 1 which is N-[4-(β-<1-butyl-1,2-dihydro-2-oxo-nicotinamido>-ethyl)-benzenesulfonyl]-N'-(4-methylcyclohexyl)-urea.

7. A method for the treatment of Diabetes mellitus which comprises administering to a host, in need of such treatment, an effective amount of a compound as defined in claim 1.

8. A method for the treatment of Diabetes mellitus wherein an effective amount in an oral dosage form from 1 to 100 mg per dose of a benzene sulfonyl urea as claimed in claim 1 or a salt thereof is administered to a host in need of such treatment.